(12) United States Patent
Wariar et al.

(10) Patent No.: US 8,417,463 B2
(45) Date of Patent: Apr. 9, 2013

(54) SYSTEMS AND METHODS FOR MONITORING PULMONARY EDEMA DYNAMICS

(75) Inventors: Ramesh Wariar, Blaine, MN (US); John D. Hatlestad, Maplewood, MN (US); Kenneth C. Beck, St. Paul, MN (US); Aaron Lewicke, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 527 days.

(21) Appl. No.: 12/505,926

(22) Filed: Jul. 20, 2009

(65) Prior Publication Data
US 2010/0022911 A1 Jan. 28, 2010

Related U.S. Application Data

(60) Provisional application No. 61/082,707, filed on Jul. 22, 2008.

(51) Int. Cl.
*A61B 5/00* (2006.01)
*A61B 5/08* (2006.01)
*A61B 5/02* (2006.01)
*A61B 5/04* (2006.01)
*A61N 1/00* (2006.01)
*G01N 33/48* (2006.01)
*G01N 33/50* (2006.01)

(52) U.S. Cl. .......... 702/19; 600/301; 600/484; 600/485; 600/547; 600/561; 607/18; 607/23

(58) Field of Classification Search .......... 600/483–488, 600/504–507, 547, 561, 300, 301; 702/187, 702/19; 607/17, 18, 23
See application file for complete search history.

(56) References Cited

U.S. PATENT DOCUMENTS

| | | | |
|---|---|---|---|
| 5,056,056 A * | 10/1991 | Gustin .......... 702/187 |
| 6,512,949 B1 | 1/2003 | Combs et al. |
| 6,970,742 B2 | 11/2005 | Mann et al. |
| 7,177,681 B2 | 2/2007 | Zhu et al. |
| 7,566,308 B2 | 7/2009 | Stahmann |
| 7,774,055 B1 * | 8/2010 | Min .......... 600/547 |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0116590 A1 * | 6/2006 | Fayram et al. .......... 600/508 |
| 2008/0139958 A1 * | 6/2008 | Uemura et al. .......... 600/547 |
| 2008/0294060 A1 | 11/2008 | Haro et al. |

* cited by examiner

*Primary Examiner* — Max Hindenburg
*Assistant Examiner* — John Pani
(74) *Attorney, Agent, or Firm* — Schwegman Lundberg & Woessner, P.A.

(57) ABSTRACT

This document discusses, among other things, systems and methods for measuring the dynamics of pulmonary congestion in heart failure subjects over time to monitor the subjects susceptibility to pulmonary edema, including sensing and receiving information indicative of a bodily pressure and information indicative of pulmonary fluid, and using the transient responses of these measurements to compute parameters related to the dynamics of thoracic fluid accumulation, such as a critical pressure ($P_c$), a critical time ($T_c$), or a filtration index ($K_{fi}$).

20 Claims, 7 Drawing Sheets

SYSTEMS AND METHODS FOR MONITORING PULMONARY EDEMA DYNAMICS

CROSS-REFERENCE TO RELATED APPLICATION

This application claims the benefit of U.S. Provisional Application No. 61/082,707, filed on Jul. 22, 2008, under 35 U.S.C. §119(e), which is hereby incorporated by reference.

TECHNICAL FIELD

This document pertains generally to medical systems, devices, or methods, and more particularly, but not by way of limitation, to systems and methods for monitoring pulmonary edema.

BACKGROUND

One hallmark of heart failure (HF) in a subject is congestion, more commonly referred to as fluid retention. Reasons for fluid retention are complex and multifactorial. Fluid retention or accumulation in the lungs or other respiratory organs (e.g., the trachea, the bronchi, etc.) is referred to as Pulmonary Edema (PE). In certain examples, fluid can accumulate in extracellular spaces, such as the spaces between lung tissue cells, commonly referred to as interstitial pulmonary edema. If left untreated, fluid can move from the extracellular space into the lung air-sacs, commonly referred to as alveolar pulmonary edema. One of the most common systems of heart failure is shortness of breath resulting from pulmonary congestion.

Although subjects with chronic heart failure can have varying levels of pulmonary congestion, they can be clinically stable most of the time without debilitating symptoms such as shortness of breath. However, fundamental changes in a disease state or other factors, such as non-compliance with diet, medication, etc., can worsen the heart failure condition, resulting in increased pulmonary congestion or edema. Although advanced pulmonary edema can be a serious or potentially fatal medical condition, it can be averted by treatment if detected early. Accordingly, various chronic ambulatory sensors and associated methods have been developed to detect the early onset of pulmonary and thoracic congestion that including cardiopulmonary pressure sensors or thoracic or lung fluid sensors. In certain examples, chronic ambulatory sensors can be used independently or in combination to detect the early onset of pulmonary congestion.

OVERVIEW

This document discusses, among other things, systems and methods for monitoring pulmonary edema, including sensing and receiving information indicative of a bodily pressure and information indicative of pulmonary fluid, and computing a critical pressure ($P_c$) using the pressure information and the pulmonary fluid information. In an example, the dynamics of pulmonary congestion in heart failure subjects can be measured over time to monitor the subjects susceptibility to pulmonary edema, including sensing and receiving information indicative of a bodily pressure and information indicative of pulmonary fluid, and using the transient responses of these measurements to compute parameters related to the dynamics of thoracic fluid accumulation, such as a critical pressure ($P_c$), a critical time ($T_c$), or a filtration index ($K_{fi}$).

In certain examples, a subject's susceptibility to pulmonary edema can depend upon microvascular factors that lead to fluid movement from lung blood vessels (pulmonary capillaries) into lung tissue. The Starling equation can be used to describe the fluid transport, and reads as follows:

$$\dot{Q}_F = K_F \cdot (\Delta P - \sigma \cdot \Delta \pi) - \dot{Q}_L \text{ where:}$$

$\dot{Q}_F$=rate of fluid filtration across capillary membrane into the lung;
$K_F$=hydraulic conductivity of the capillary membrane;
$\Delta P$=transmembrane hydrostatic pressure difference;
$\sigma$=osmotic reflection coefficient;
$\Delta \pi$=transmembrane oncotic pressure difference; and
$\dot{Q}_L$=lymphatic flow rate.

A hydrostatic driving pressure difference, $\Delta P$, is the primary driving force for fluid filtration from the pulmonary capillaries into the lungs. However, since proteins do not readily move across the blood, some of the filtered fluid is reabsorbed by the oncotic force of the blood (denoted by the term—$\sigma \cdot \Delta \pi$). The term $K_F$ denotes the hydraulic conductivity which is a biophysical measure of the hydraulic resistance to fluid flow. Any net fluid that then enters the interstitial space of the lung can be removed by the lymphatic system.

A simplified example of the utility of the Starling equation is provided for illustrative purposes. Subjects having chronic heart failure generally retain more fluid than normal subjects, which causes the $\Delta P$ to be greater and the $\Delta \pi$ to be lower. Over time, these subjects' pulmonary systems can compensate by increasing $K_F$ (related to a thickening of their lung basement membrane) and $\dot{Q}_L$ (increased lymphatic flow). In these subjects, a worsening heart failure episode results when $\dot{Q}_L$ is unable to increase (e.g., when $\dot{Q}_L$ becomes saturated) in the face of increases in $\Delta P$. Thus, a subject who is stable but operating closer to his $\dot{Q}_{Lmax}$ is more susceptible to pulmonary edema. The present inventors have recognized, among other things, that the susceptibility can be detected, measured, and trended over time.

In Example 1, a system includes a pressure sensor configured to sense information indicative of a bodily pressure, a fluid sensor configured to sense information indicative of pulmonary fluid, and a processor, communicatively coupled to the pressure sensor and the fluid sensor, the processor configured to receive pressure information and pulmonary fluid information, and wherein the processor is configured to compute a critical pressure ($P_c$) using the pressure information and the pulmonary fluid information, wherein the critical pressure ($P_c$) is the pressure at which the pulmonary fluid information is indicative of an increase in pulmonary fluid.

In Example 2, the processor of Example 1 is optionally configured to generate a pulmonary fluid baseline using the pulmonary fluid information, and wherein the critical pressure ($P_c$) includes the pressure at which the pulmonary fluid information deviates from the pulmonary fluid baseline, wherein the deviation is indicative of an increase in pulmonary fluid.

In Example 3, the fluid sensor of any one or more of Examples 1-2 optionally includes an impedance sensor and the information indicative of the pulmonary fluid of any one or more of Examples 1-2 optionally includes an impedance, wherein the pulmonary fluid baseline of any one or more of Examples 1-2 optionally includes an impedance baseline, and wherein the critical pressure ($P_c$) of any one or more of Examples 1-2 optionally includes the pressure at which the impedance falls below the impedance baseline.

In Example 4, the system of any one or more of Examples 1-3 optionally includes an event detector coupled to the processor, the event detector configured to detect a pulmonary fluid overload event, wherein the processor of any one or more of Examples 1-3 is optionally configured to compute the critical pressure ($P_c$) using the pressure information and the pulmonary fluid information sensed leading up to or during the detected event.

In Example 5, the processor of any one or more of Examples 1-4 is optionally configured to generate a pressure baseline using the pressure information, and wherein the processor of any one or more of Examples 1-4 is optionally configured to compute a critical time ($T_c$) using the pressure information and the pulmonary fluid information, wherein the critical time ($T_c$) includes a duration beginning when the pressure information deviates from the pressure baseline and ending when the pressure reaches the critical pressure ($P_c$).

In Example 6, the system of any one or more of Examples 1-5 optionally includes an event detector coupled to the processor, the event detector configured to detect a pulmonary fluid overload event, wherein the processor of any one or more of Examples 1-5 is optionally configured to compute the critical time ($T_c$) using the pressure information and the pulmonary fluid information sensed leading up to or during the detected event.

In Example 7, the processor of any one or more of Examples 1-6 is optionally configured to compute an estimated critical time ($T_{ec}$), wherein the estimated critical time ($T_{ec}$) is an estimated time until the pressure reaches the critical pressure ($P_c$), and wherein the processor of any one or more of Examples 1-6 is optionally configured to compute the estimated critical time ($T_{ec}$) using the pressure information and the difference between the pressure information and the critical pressure ($P_c$).

In Example 8, the processor of any one or more of Examples 1-7 is optionally configured to compute an estimated decompensation time ($T_{ed}$), wherein the estimated decompensation time ($T_{ed}$) is an estimated time until the pulmonary fluid information is indicative of the pulmonary fluid associated with a previous pulmonary fluid overload event, and wherein the processor of any one or more of Examples 1-7 is optionally configured to compute the estimated decompensation time ($T_{ed}$) using the pulmonary fluid information and the difference between the pulmonary fluid information and the pulmonary fluid associated with the previous pulmonary fluid overload event.

In Example 9, the processor of any one or more of Examples 1-8 is optionally configured to compute a filtration index ($K_{fi}$) as a function of a slope of the pressure information and a slope of the pulmonary fluid information.

In Example 10, the system of any one or more of Examples 1-9 optionally includes an event detector coupled to the processor, the event detector configure to detect a pulmonary fluid overload event, wherein the processor of any one or more of Examples 1-9 is optionally configured to compute the filtration index ($K_{fi}$) using the pulmonary artery pressure information and the pulmonary fluid information sensed leading up to or during the detected event.

In Example 11, the event of any one or more of Examples 1-10 optionally includes at least one of a user-confirmed pulmonary fluid overload event or an automatically detected pulmonary fluid overload event, wherein the user-confirmed event includes at least one of a hospitalization or a change in medication, and wherein the automatically detected event includes at least one of information exceeding a threshold or a baseline, the information including at least one of a value or a slope.

In Example 12, the pressure sensor of any one or more of Examples 1-11 optionally includes an implantable chronic pulmonary artery pressure sensor configured to chronically sense information indicative of a pulmonary artery pressure of a pulmonary artery, and wherein the implantable chronic pulmonary artery pressure sensor is configured to be fixed to a location within the pulmonary artery.

In Example 13, the processor of any one or more of Examples 1-12 is optionally configured to provide a critical pressure ($P_c$) alert to a user when the pressure information is indicative that the pressure is approaching the critical pressure ($P_c$) or that the critical pressure ($P_c$) has been reached.

In Example 14, the system of any one or more of Examples 1-13 optionally includes a display, communicatively coupled to the processor, the display configured to receive at least one of the pressure information, the pulmonary fluid information, or the critical pressure ($P_c$) from the processor and provide information to a user.

In Example 15, a method includes receiving information indicative of a bodily pressure, receiving information indicative of pulmonary fluid, and computing a critical pressure ($P_c$) using the pressure information and the pulmonary fluid information, wherein the critical pressure ($P_c$) is the pressure at which the pulmonary fluid information is indicative of an increase in pulmonary fluid.

In Example 16, the method of Example 15 optionally includes generating a pulmonary fluid baseline, wherein the computing the critical pressure ($P_c$) includes computing a pressure at which the pulmonary fluid information deviates from the pulmonary fluid baseline, wherein the deviation is indicative of an increase in pulmonary fluid.

In Example 17, the method of any one or more of Examples 15-16 optionally includes detecting a pulmonary fluid overload event, wherein the computing the critical pressure ($P_c$) includes using the pressure information and the pulmonary fluid information sensed leading up to or during the detected event.

In Example 18, the method of any one or more of Examples 15-17 optionally includes generating a pressure baseline, and computing a critical time ($T_c$) using the pressure information and the pulmonary fluid information, wherein the computing the critical time ($T_c$) includes computing a duration beginning when the pressure information deviates from the pressure baseline and ending when the pressure reaches the critical pressure ($P_c$).

In Example 19, the method of any one or more of Examples 15-18 optionally includes detecting a pulmonary fluid overload event, wherein the computing the critical time ($T_c$) includes using the pressure information and the pulmonary fluid information sensed leading up to or during the detected event.

In Example 20, the method of any one or more of Examples 15-19 optionally includes computing an estimated critical time ($T_{ec}$), wherein the estimated critical time ($T_{ec}$) is an estimated time until the pressure reaches the critical pressure ($P_c$), and wherein the computing the estimated critical time ($T_{ec}$) includes using the pressure information and the difference between the pressure information and the critical pressure ($P_c$).

In Example 21, the method of any one or more of Examples 15-20 optionally includes computing an estimated decompensation time ($T_{ed}$), wherein the estimated decompensation time ($T_{ed}$) is an estimated time until the pulmonary fluid information is indicative of the pulmonary fluid associated with a previous pulmonary fluid overload event, and wherein the computing the estimated decompensation time ($T_{ed}$) of any one or more of Examples 15-20 optionally includes using the pulmonary fluid information and the difference between the pulmonary fluid information and the pulmonary fluid associated with the previous pulmonary fluid overload event.

In Example 22, the method of any one or more of Examples 15-21 optionally includes computing a filtration index ($K_{fi}$) as a function of a slope of the pressure information and a slope of the pulmonary fluid information.

In Example 23, the method of any one or more of Examples 15-22 optionally includes detecting a pulmonary fluid overload event, and wherein the computing the filtration index ($K_{fi}$) of any one or more of Examples 15-22 optionally includes using the pressure information and the pulmonary fluid information sensed leading up to or during the detected event.

In Example 24, the detecting the pulmonary fluid overload event of any one or more of Examples 15-23 optionally includes detecting at least one of a user-confirmed pulmonary fluid overload event or an automatically detected pulmonary fluid overload event, wherein the user-confirmed event of any one or more of Examples 15-23 optionally includes at least one of a hospitalization or a change in medication, and wherein the automatically detected event includes at least one of information exceeding a threshold or a baseline, the information including at least one of a value or a slope.

In Example 25, the method of any one or more of Examples 15-24 optionally includes at least one of providing a critical pressure ($P_c$) alert to a user when the pressure information is indicative that the pressure is approaching the critical pressure ($P_c$) or that the critical pressure ($P_c$) has been reached, or providing at least one of the pressure information, the pulmonary fluid information, or the critical pressure ($P_c$) to a user.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In an example, the present inventors have recognized, among other things, systems and methods for monitoring long-term changes in susceptibility to pulmonary edema in congestive heart failure subjects.

In certain examples, a hallmark of chronic heart failure can include pulmonary congestion and subject hospitalization for pulmonary edema. Pulmonary edema can result from a failure of a subject's pulmonary compensatory mechanisms to maintain a fluid balance in at least a portion of the body.

In an example, the availability of chronic sensor for measuring pulmonary artery pressure and lung fluid enables trending of parameters extracted from the kinetics of pulmonary congestion, such as critical pressure and time to compensatory failure. In certain examples, these trends can be used to tailor algorithms for decompensation detection or long-term monitoring of heart failure status in response to certain factors, such as subject medication or lifestyle change.

In an example, the lungs of a subject having chronic heart failure can tolerate higher than normal pulmonary artery pressure without edema due to certain factors, including decreased water permeability from fibrosis of the pulmonary microvasculature, or increased lymphatic flow rates. During cardiac decompensation, these local pulmonary compensatory mechanisms can be overwhelmed leading to the subject being hospitalized for pulmonary edema.

The present inventors have recognized, among other things, that recent advancements in chronic measurements of pulmonary edema kinetics, such as pulmonary artery pressure monitoring and transthoracic impedance monitoring, can allow for trending of parameters derived from thoracic fluid accumulation dynamics, from which the susceptibility of the lung to edema can be determined.

Figure 1:
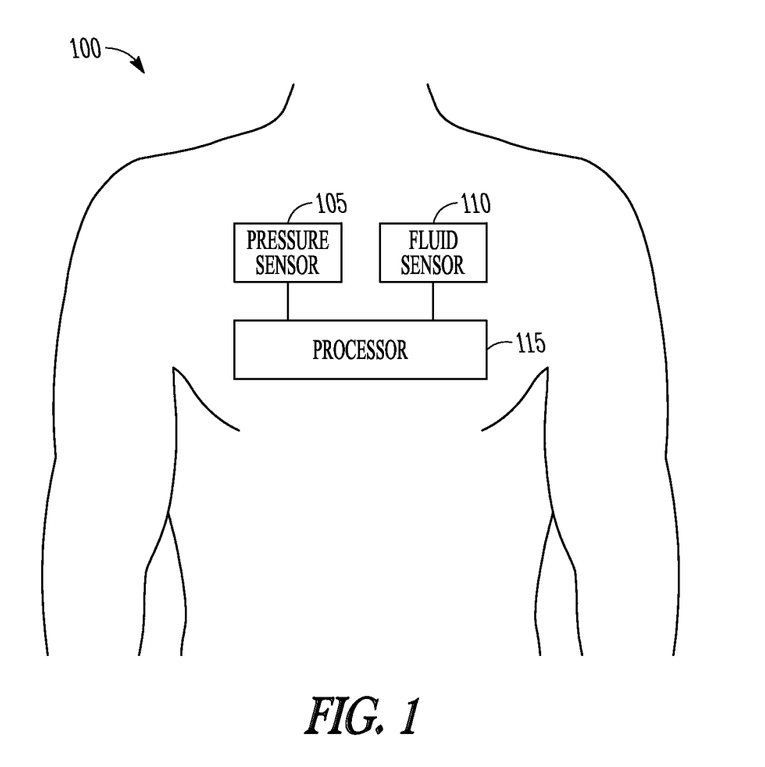
FIG. 1 illustrates generally an example of a system including a pressure sensor, a fluid sensor, and a processor.

FIG. 1 illustrates generally an example of a system 100 including a pressure sensor 105 and a fluid sensor 110, each communicatively coupled to a processor 115.

In certain examples, the pressure sensor 105 can include a pulmonary artery pressure sensor, a right ventricular pressure sensor, a left atrial pressure sensor, or other implantable or external pressure sensor configured to sense information indicative of a bodily pressure (e.g., a thoracic pressure). In an example, the pressure sensor 105 can include a pulmonary artery pressure sensor configured to sense the driving force of blood through the pulmonary artery, such as an implantable pressure sensor configured to be located in a pulmonary artery of a subject.

In an example, the fluid sensor 110 can include a pulmonary, thoracic, or other fluid sensor configured to sense information indicative of or correlated to fluid in the lungs, thorax, or other portion of the body. In certain examples, the fluid sensor 110 can include an intrathoracic total impedance (ITTI) sensor or other thoracic or other impedance sensor (e.g., a lead impedance sensor, a minute ventilation sensor, etc.) or other sensor configured to sense a parameter (e.g., impedance or other parameter) indicative of pulmonary fluid. In other examples, the fluid sensor 110 can include a hematocrit based fluid sensor, an ultrasound based fluid sensor, or other implantable or external fluid sensors configured to sense or receive measurements based on acoustic, thermal, optical, one or more displacement property of various tissue in the thorax, or a transit time of one or more markers in the lungs or thorax.

In various examples, the processor 115 can be an implantable component (e.g., an implantable cardiac rhythm management device or other implantable component), an external component (e.g., a patient or clinician controlled medical device programmer, a repeater, an external processor, or other external component), or a combination or permutation of an implantable component and an external component.

In an example, the pressure sensor 105 can include a pressure sensor configured to sense a pulmonary artery pressure signal of the pulmonary artery of the subject. The pulmonary artery pressure signal can include any signal indicative of the pulmonary artery pressure of the pulmonary artery of the subject, such as a systolic pressure, a diastolic pressure, a mean pressure, etc. In an example, the pulmonary artery pressure sensor 105 can be configured to produce a pulmonary artery pressure signal, such as an electrical, mechanical, or optical pulmonary artery pressure signal, that can include information about the pulmonary artery pressure of the pulmonary artery of the subject. In certain examples, the pressure sensor 105 can include a chronic pulmonary artery pressure sensor configured to be implanted into the pulmonary artery of the subject and remain in the pulmonary artery for a continuing or extended period of time (e.g., months, years, etc.).

The pressure sensor 105 can include a chronic non-lead-based pressure sensor (e.g., a pressure sensor being held in the pulmonary artery without the aid of catheter, lead, or other tethered anchor). In certain examples, the non-lead-based pressure sensor can be implemented as a stand-alone device, with or without another implantable medical device, such as a pacemaker, defibrillator, or other implantable cardiac rhythm management or implanted medical device. The non-lead-based pressure sensor can be configured to be located at a close proximity to the left side of the heart, such as within the pulmonary artery, to receive a physiologic signal, e.g., indicative of a pressure or a flow within the pulmonary artery, at a close proximity to the left side of the heart.

In other examples, the pressure sensor 105 can include an implantable pressure sensor placed in the pulmonary artery to sense the pulmonary artery pressure signal, such as that disclosed in the commonly assigned Stahmann U.S. patent application Ser. No. 11/249,624 entitled "METHOD AND APPARATUS FOR PULMONARY ARTERY PRESSURE SIGNAL ISOLATION," which is hereby incorporated by reference in its entirety, including its disclosure of sensing the pulmonary artery pressure signal using the implantable pressure sensor placed in the pulmonary artery. In other examples, other pressure sensor configurations can be used to sense the pulmonary artery or other pressure signal.

In an example, the pressure sensor 105 can be configured to communicate with one or more than one implantable medical device (IMD), such as the processor 115, a cardiac rhythm management device, an external medical device, or a combination or permutation of the one or more than one IMD, the processor 115, the cardiac rhythm management device, and the external medical device. Certain examples of such sensors, sensor configurations, and communication systems and methods are discussed in more detail in the Mazar et al. U.S. patent application Ser. No. 10/943,626 entitled "SYSTEMS AND METHODS FOR DERIVING RELATIVE PHYSIOLOGIC PARAMETERS;" the Von Arx et al. U.S. patent application Ser. No. 10/943,269 entitled "SYSTEMS AND METHODS FOR DERIVING RELATIVE PHYSIOLOGIC MEASUREMENTS USING AN EXTERNAL COMPUTING DEVICE;" the Von Arx et al. U.S. patent application Ser. No. 10/943,627 entitled "SYSTEMS AND METHODS FOR DERIVING RELATIVE PHYSIOLOGIC PARAMETERS USING A BACKEND COMPUTING SYSTEM;" and the Chavan et al. U.S. patent application Ser. No. 10/943,271 entitled "SYSTEMS AND METHODS FOR DERIVING RELATIVE PHYSIOLOGIC PARAMETERS USING AN IMPLANTED SENSOR DEVICE;" and the U.S. patent application Ser. No. 10/943,271 entitled "SYSTEMS AND METHODS FOR DERIVING RELATIVE PHYSIOLOGIC MEASUREMENTS USING AN IMPLANTED SENSOR DEVICE," all assigned to Cardiac Pacemakers, Inc., all of which are incorporated herein by reference in their entirety, and which are collectively referred to as the "Physiologic Parameter Sensing Systems and Methods Patents" in this document.

In an example, the fluid sensor 110 can be configured to sense a fluid signal, such as a pulmonary fluid signal of a lung or other respiration organ or pulmonary anatomy of the subject or other fluid signal. The fluid signal can include any signal indicative of a status, amount, volume, level, density, or other parameter or characteristic of the cardiopulmonary system or other fluid of a lung or other respiratory organ, pulmonary anatomy, or other organ or location of the subject. In an example, the fluid sensor 110 can be configured to produce a fluid signal, such as an electrical, mechanical, or optical pulmonary or other fluid signal, that can include information about the pulmonary or other fluid status of the subject. In certain examples, the information about the fluid status can include information about at least one of a pulmonary fluid amount, a pulmonary fluid volume, a pulmonary fluid level, a pulmonary fluid density, or other fluid amount, volume, level, density, etc.

In an example, the fluid sensor 110 can include a thoracic impedance sensor, such as that disclosed in the commonly assigned Zhu et al. U.S. Pat. No. 7,177,681 entitled "Cardiac rhythm management system for edema," which is hereby incorporated by reference in its entirety, including its disclosure of detecting a thoracic impedance of a subject and comparing the thoracic impedance to a baseline thoracic impedance. In other examples, other pulmonary or other fluid sensors or sensor configurations can be used to sense the fluid signal.

In the example of FIG. 1, the processor 115 can be communicatively coupled to the pressure sensor 105. In certain examples, the processor 115 can be an implantable component, an external component, or a combination or permutation of an implantable and an external component (e.g., an implantable communication device communicatively coupled to the pressure sensor 105 or the fluid sensor 110 configured to communicate with an external processor, etc.) The processor 115 can be configured to receive information from the pressure sensor 105, such as discussed in more detail in the Physiologic Parameter Sensing Systems and Methods Patents, as well as receive information from the fluid sensor 110. In certain examples, one or more of the techniques discussed in the Physiologic Parameter Sensing Systems and Methods Patents can be used to receive information from the fluid sensor 110. Generally, the processor 115 can be configured to receive physiological information from a subject using one or more sensor and compute an indication of edema in the subject or one or more parameter related to pulmonary edema dynamics, such as an indication of the onset of edema, a critical pressure, a critical time, a filtration index, or other pressure or fluid points using the received information. In certain examples, the processor 115 can be configured to store information received from or derived from the pressure sensor 105 or the fluid sensor 110, or the processor 115 can be configured to communicate the received or derived information to an external location, such as a central or other external computing system, e.g., for further processing or storage.

In an example, the processor 115 can be configured to compute a critical pressure ($P_c$) using the pressure information received from the pressure sensor 105 and the pulmonary fluid information received from the fluid sensor 110. The critical pressure ($P_c$) can include the pressure at which the pulmonary fluid information is indicative of an increase in pulmonary fluid. In an example, the pulmonary fluid information can include an impedance, such as a thoracic impedance, an intra thoracic total impedance, or other impedance. In an example, the critical pressure ($P_c$) can include the pressure at which the impedance deviates (e.g., falls below) from a baseline impedance. In certain examples, the baseline impedance can include a filtered impedance value, such as an impedance value computed using one or more curve fitting techniques or other filtering techniques. In other examples, other baselines can be computed using other pulmonary fluid information. In an example, once the impedance value or other value indicative of pulmonary fluid information deviates from the baseline impedance or other baseline (e.g., deviates by a desired amount or percentage), the critical pressure ($P_c$) can be computed.

In other examples, the processor 115 can be configured to compute a critical time ($T_c$) using the pressure information and the pulmonary fluid information. In an example, the computation of critical time ($T_c$) can include any time duration where the pressure information and the pulmonary fluid information are indicative of increases in a pressure and a pulmonary fluid in response to a known or detected fluid overload event, whether natural or through drug withdrawal. In an example, the critical time ($T_c$) computation can include a time period beginning when the pressure information deviates (e.g., rises above) a baseline pressure (e.g., a pulmonary pressure baseline or other pressure information baseline), and ending when the pulmonary fluid information deviates from a baseline pulmonary fluid value.

Figure 2:
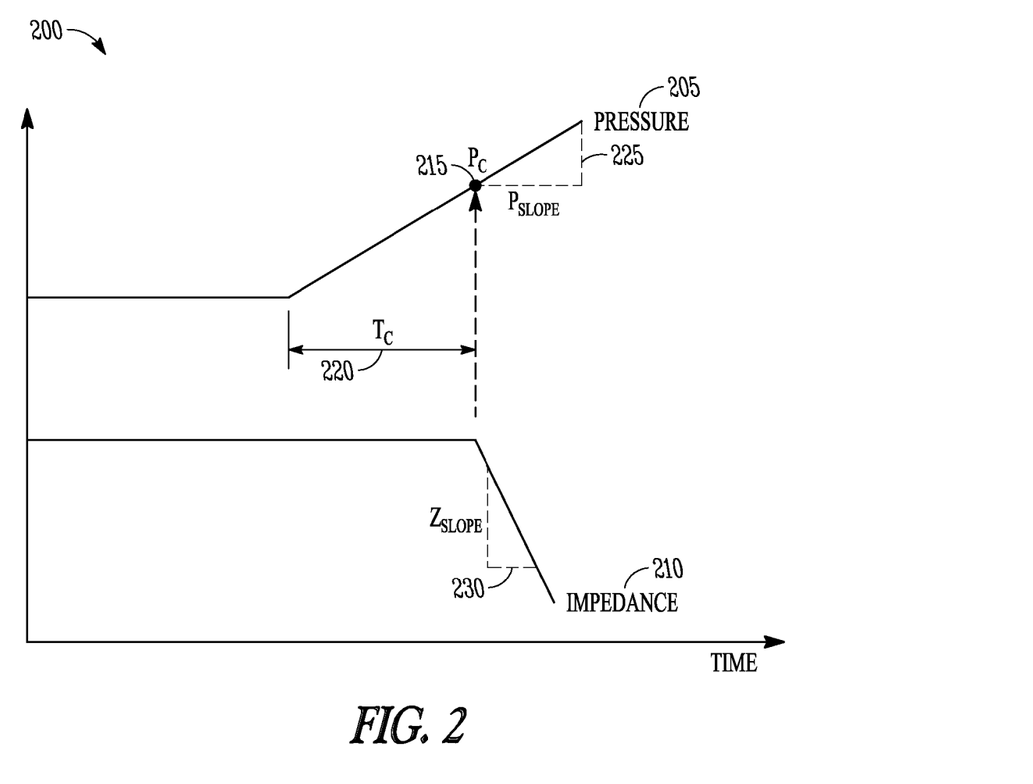
FIG. 2 illustrates generally an example of a relationship between a pressure signal and an impedance signal.

In an example, the processor 115 can be configured to compute a filtration index ($K_{fi}$) using the pressure information and the pulmonary fluid information. In certain examples, the filtration index ($K_{fi}$) can be a function of a slope of the pressure information and a slope of the pulmonary fluid information, once each of the pressure information and the pulmonary fluid information have deviated from their respective baselines, as shown in FIG. 2, and as illustrated in Eq. 1 below:

$$K_f = \frac{ZSlope}{PSlope} \quad (Eq.\ 1)$$

In other examples, the processor 115 can be configured to calculate or monitor other pressure, fluid, or other points or metrics using the received information. In certain examples, processor 115 can be configured to monitor the received information, the critical pressure ($P_c$), the critical time ($T_c$), the filtration index ($K_{fi}$), or other parameters or metrics associated with or sensitive to pulmonary compensation mechanisms with a short-term emphasis, a long-term emphasis, or combination of both short and long-term emphasis. In an example, with the short-term emphasis, the processor 115 can be configured to monitor the received information for acute or abrupt changes in status or fluctuations of received information.

In an example, the processor 115 can be configured to monitor the pressure information, the pulmonary fluid information, or other physiological information over time. In certain examples, the processor 115 can be configured to create one or more trends using the received information, such as a pressure trend, a pulmonary fluid trend, a critical pressure trend, etc. In various examples, the one or more trends can be used to compute the critical pressure ($P_c$), the critical time ($T_c$), the filtration index ($K_{fi}$), or one or more other parameter related to pulmonary edema dynamics. In other examples, changes in the one or more parameters or received information can be used as an indication of a progression or deterioration of a physiological status, to initiate clinician or other intervention, to change one or more remote monitoring or other thresholds, etc.

FIG. 2 illustrates generally a relationship 200 between a pressure signal 205 and an impedance signal 210. When a physiological event leads to pulmonary fluid volume overload, a pulmonary artery pressure or other pressure can increase (shown as the pressure signal 205) followed, after a period of time, by an increase in pulmonary fluid in one or both lungs (shown as the impedance signal 210). In this example, the accumulation of fluid in one or both lungs can be shown as a decrease in detected impedance. A delay in the accumulation of fluid, in this example a critical time ($T_c$) 220, can reflect the amount of time to failure of the pulmonary compensatory mechanisms of the body, such as lymphatic flow. Similarly, a critical pressure, e.g. a critical pressure ($P_c$) 215, can be detected as the pressure (e.g., the pulmonary artery pressure) at which the decrease in impedance (or increase in pulmonary fluid) is sensed. In an example, the critical pressure ($P_c$) 215 can mark the point at which the pulmonary compensation of the body fails. Further, because the lungs of a chronic heart failure subject can tolerate higher than normal pulmonary artery pressure without edema, the critical pressure at which pulmonary compensation fails can be different for each subject and can be different at varying stages of a subject's health (e.g., as a subject's heart failure status gradually worsens, the subject's critical pressure can increase). In certain examples, the critical pressure ($P_c$) 215 can be calculated as a function of lymphatic flow saturation, increased fibrosis, or other physiologic condition. Further, a filtration index ($K_{fi}$) can be calculated using the pressure signal 205 and the impedance signal 210 as a function of a slope of the pressure signal 205, PSlope 225, and as a slope of the impedance signal 210, ZSlope 230. In an example, the filtration index ($K_{fi}$) can be indicative of the severity of a pulmonary fluid overload event, and can be used to compare one or more detected events with each other or other clinical or subject-specific information.

Figure 3:
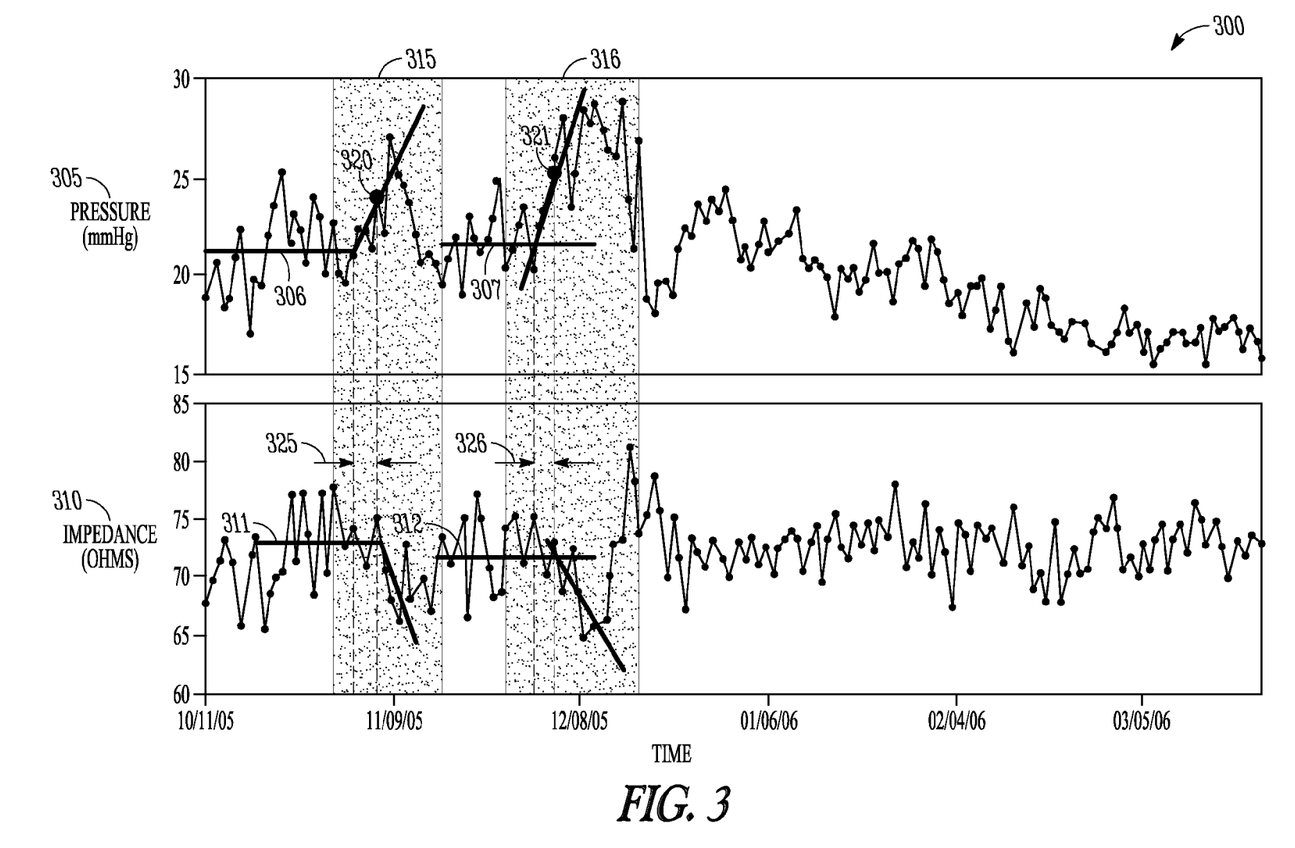
FIG. 3 illustrates generally an example of clinical data illustrating a relationship between a pressure signal and an impedance signal.

FIG. 3 illustrates generally an example of clinical data illustrating a relationship 300 between a pressure signal 305 and an impedance signal 310. In the example of FIG. 3, two events are identified, a first event 315 (a first fluid overload or hypervolemia) and a second event 316 (a second fluid overload or hypervolemia). In this example, a first representation of the pressure signal 306 is shown for the first event 315 having two portions, a baseline flat portion leading into the first event 315, and a portion moving upwards during the first event 315. In an example, these two portions of the first representation of the pressure signal 306, as well as others, can be generated using one or more filtering techniques, such as a curve fitting technique. Similarly, a second representation of the pressure signal 307 is shown for the second event 316 having two similar portions. Further, in this example, a first representation of the impedance signal 311 is shown for the first event 315 having two portions, a baseline flat portion leading into the first event 315, and a portion moving downwards during the first event 315. Similarly, a second representation of the impedance signal 312 is shown for the second event 316 having two similar portions.

In this example, a first critical point ($P_c$) 320 is identified as the point of the first representation of the pressure signal 306 at which the first representation of the impedance signal 311 deviates from its baseline first portion. Further, in this example, a second critical point ($P_c$) 321 is identified as the point of the second representation of the pressure signal 307 at which the second representation of the impedance signal 312 deviates from its baseline first portion. Moreover, in this example, a first critical time ($T_c$) 325 and a second critical time ($T_c$) 326 are identified as the time period between the transitions from the first portion of the first representation of the pressure signal 306 and the first portion of the first representation of the impedance signal 311, and the first portion of the second representation of the pressure signal 307 and the first portion of the second representation of the impedance signal 312, respectively.

In other examples, raw data or histogram data, such as the pressure signal 305 or the impedance signal 310 of FIG. 3, can be received, for example, from a pressure sensor, a fluid sensor, or other physiological sensor, and then transmitted for external or other processing use, e.g., outside the components shown in FIG. 1.

Figure 4:
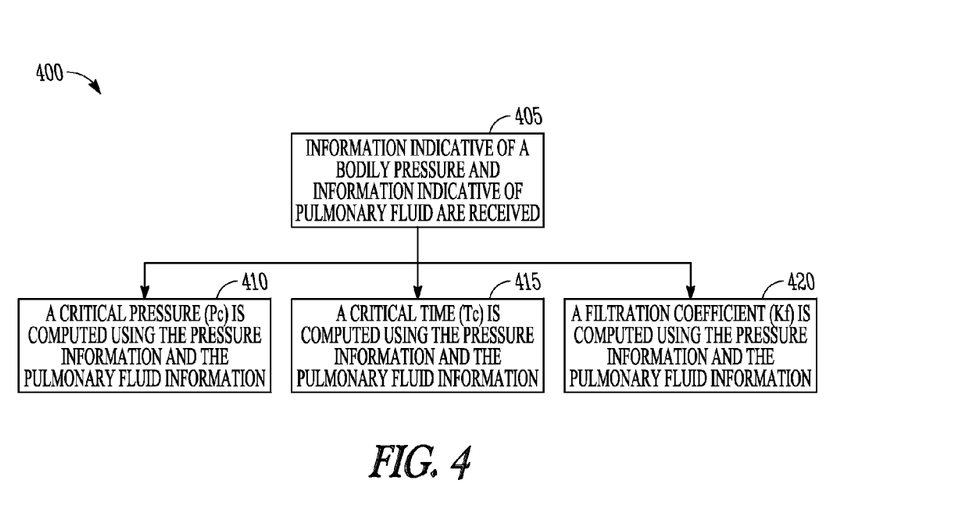
FIG. 4 illustrates generally an example of a method including computing a critical pressure ($P_c$), a critical time ($T_c$), and a filtration index ($K_{fi}$) using pressure information and pulmonary fluid information.

FIG. 4 illustrates generally an example of a method 400 including computing a critical pressure ($P_c$), a critical time ($T_c$), and a filtration index ($K_{fi}$) using pressure information and pulmonary fluid information.

At 405, information indicative of a bodily pressure and information indicative of pulmonary fluid are received. In an example, the information indicative of a bodily pressure can be sensed using a pressure sensor, e.g., the pressure sensor 105, and the information indicative of pulmonary fluid can be sensed using a fluid sensor, e.g., the fluid sensor 110. The information indicative of a bodily pressure and information indicative of pulmonary fluid can be received at a processor, e.g., the processor 115.

In an example, raw data indicative of a bodily pressure or pulmonary fluid can be received, e.g., from one or more implantable or external sensors. In other examples, processed, selected, or other data indicative of a bodily pressure or pulmonary fluid can be received. In an example, the received raw data can be filtered or otherwise processed to obtain baseline or other averaged, filtered, or other stable information. For example, FIG. 2 illustrates examples of processed information. Further, FIG. 3 illustrates one example of raw data indicative of a bodily pressure and pulmonary fluid, as well as processed data (in this example, curve fitting techniques).

At 410, a critical pressure ($P_c$) is computed using the pressure information and the pulmonary fluid information. In an example, the critical pressure ($P_c$) can be computed using a processor, e.g., the processor 115. In an example, the critical pressure ($P_c$) can include the pressure at which the pulmonary fluid information is indicative of an increase in pulmonary fluid.

In the example of FIG. 3, the pulmonary fluid information includes the impedance signal 310, and the pressure information includes the pressure signal 305. As seen in FIG. 3, the impedance signal 310 and the pressure signal 305 constantly vary, increasing and decreasing. However, once the impedance signal 310 and the pressure signal 305 has been processed, filtered, or otherwise trended or indexed (e.g., the first representation of the pressure signal 306, the second representation of the pressure signal 307, the first representation of the impedance signal 311, the second representation of the impedance signal 312, etc.), the short term changes can be removed, and instead, long term changes or trends can be used to determine actual increases in pulmonary fluid.

In other examples, other physiological data can be received, such as activity, temperature, or other physiological or subject information to remove fluctuations that can be accounted for, such as changes in posture, physical status, time-of-day, etc.

In an example, once the pulmonary fluid information has been processed, the point at which the pulmonary fluid information is indicative of an increase in pulmonary fluid can be determined. In an example, the critical pressure ($P_c$) can include the pressure at which the increase in pulmonary fluid is determined.

In an example, the critical pressure ($P_c$) can be stored or used to alert a subject, clinician, or other user of a pressure at which treatment is required to prevent fluid overload in the patient. Further, an index or trend of the critical pressure ($P_c$) can be stored or computed, providing an accurate or updated disease state or status progression or deterioration.

At 415, a critical time ($T_c$) is computed using the pressure information and the pulmonary fluid information. In an example, the critical time ($T_c$) can be computed using a processor, e.g., the processor 115. In an example, the critical time ($T_c$) can include a time interval between when the pressure information is indicative of an increase in pressure and ending when the pressure reaches the critical pressure ($P_c$).

In an example, the point at which the pressure information is indicative of an increase in pressure can be determined like above for determining the point at which the pulmonary fluid information is indicative of an increase in pulmonary fluid. Once the increase in pressure is determined, a critical time ($T_c$) can be computed as the time period between the increase in pressure and the time the pressure reaches the critical pressure ($P_c$).

In various examples, the critical time ($T_c$) can be stored or used to alert a subject, clinician, or other user of a time period before hospitalization or other treatment is required. Further, an index or trend of the critical time ($T_c$) can be stored or computed, providing an accurate or updated estimate of time before treatment is required, or to show disease state or status progression or deterioration.

At 420, a filtration index ($K_{fi}$) is computed using the pressure information and the pulmonary fluid information. In an example, the filtration index ($K_{fi}$) can be computed using a processor, e.g., the processor 115. In an example, the filtration index ($K_{fi}$) can be computed as a function of a slope of the pressure information and a slope of the pulmonary fluid information. Further, the computed filtration index ($K_{fi}$) computation can include an index indicative of a filtration index ($K_{fi}$) computed using the information indicative of the bodily pressure, the information indicative of the pulmonary fluid, or other physiological information.

In other examples, other pulmonary edema dynamics can be calculated, e.g., using the received information indicative of a bodily pressure or the received information indicative of pulmonary fluid.

Further, one or more index or trends can be computed or stored using the received information, such as a pressure index, histogram, or trend, a pulmonary fluid index, histogram, or trend, a critical pressure ($P_c$) index, histogram, or trend, a critical time ($T_c$) index, histogram, or trend, a filtration index ($K_{fi}$), histogram, or trend, or one or more other pulmonary edema dynamics index, histogram, or trend, such as a relationship between one or more of the above metrics or other physiological information.

Figure 5:
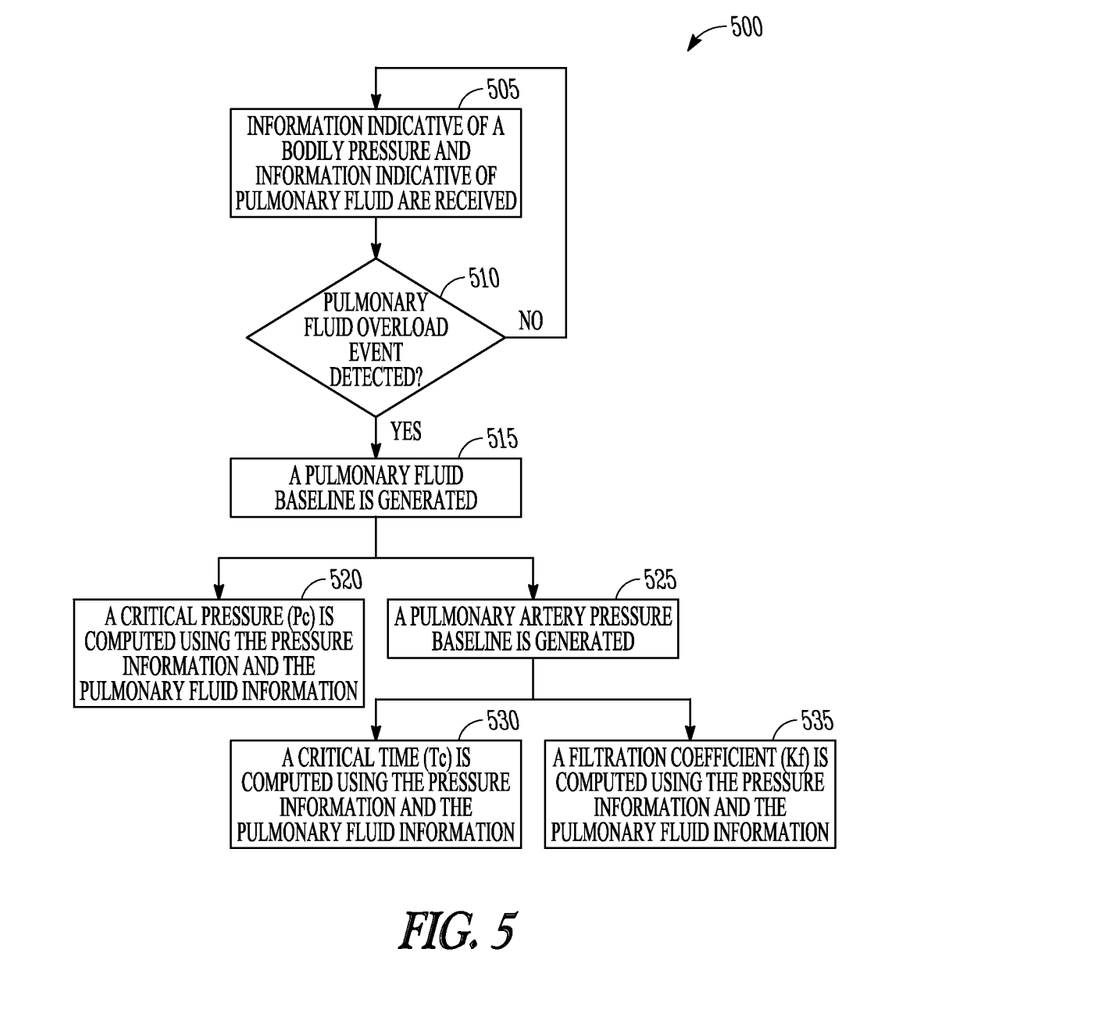
FIG. 5 illustrates generally an example of a method including detecting a pulmonary fluid overload event and generating a pulmonary fluid baseline and a pulmonary artery pressure baseline.

FIG. 5 illustrates generally an example of a method 500 including detecting a pulmonary fluid overload event and generating a pulmonary fluid baseline and a pressure baseline.

At 505, information indicative of a bodily pressure and information indicative of pulmonary fluid are received.

At 510, if a pulmonary fluid overload event is detected, then, at 515, a pulmonary fluid baseline is generated. In certain examples, the pulmonary fluid overload event can include a user-confirmed or user-detected pulmonary fluid overload event (e.g., a hospitalization, a change in medication, etc.) or an automatically detected pulmonary fluid overload event. The automatically detected event can include pressure or pulmonary fluid information (e.g., a pressure value, slope, or trend, a pulmonary fluid value, slope, or trend, a combination of pressure and pulmonary fluid information, etc.) reaching, exceeding, or approaching a threshold or a baseline. In other examples, other indications can be used to detect the pulmonary fluid overload event. In an example, if, at 510, a pulmonary fluid overload event is detected, then, at 515, a pulmonary fluid baseline can be generated using information sensed or received leading up to or during the detected event.

In an example, pulmonary fluid information can be received and stored in a buffer or a memory to be used following the detection of a pulmonary fluid overload event. If no event is detected, then the buffer or memory can be erased, or the previously stored information can be overwritten with subsequently received pulmonary fluid information. In other examples, the pulmonary fluid information can be transferred to a remote processor or programmer for further analysis.

At 515, a pulmonary fluid baseline is generated. In an example, the pulmonary fluid baseline can be generated using a processor, e.g., the processor 115. The pulmonary fluid baseline can include a processed baseline. In certain examples, various processing can be performed on the pulmonary fluid information to generate the pulmonary fluid baseline, such as averaging, filtering, a curve-fitting, regression (e.g., linear regression), or other processing to generate a baseline. The example of FIG. 3 illustrates a pulmonary fluid baseline generated using curve fitting. In other examples, other processing can be performed to generate the pulmonary fluid baseline.

If, at 510, a pulmonary fluid overload event is not detected, then a pulmonary fluid baseline is not generated, and process flow returns to step 505 where information indicative of a bodily pressure and information indicative of pulmonary fluid are received.

At 520, a critical pressure ($P_c$) is computed using the pressure information and the pulmonary fluid information. In an example, the computing the critical pressure ($P_c$) can include computing the pressure at which the pulmonary fluid information deviates from the pulmonary fluid baseline, wherein the deviation is indicative of an increase in pulmonary fluid.

In certain examples, the pulmonary fluid information can deviate from the pulmonary fluid baseline without the deviation being indicative of an increase in pulmonary fluid. For example, in the example of FIG. 3, the pulmonary fluid information includes the impedance signal 310 and the pulmonary fluid baseline includes the first representation of the impedance signal 311. In this example, the impedance signal 310 constantly varies above and below the pulmonary fluid baseline. However, the pulmonary fluid information does not vary from the baseline until the long-term change or trend is indicative of an increase in pulmonary fluid, and the first representation of the impedance signal 311 begins to deviate from its established baseline. At 520, the critical pressure ($P_c$) includes the pressure at which the pulmonary fluid information deviates from its established baseline.

At 525, a pressure baseline is generated. In an example, the pressure baseline can be generated using a processor, e.g., the processor 115. In certain examples, various processing can be performed on the pressure information to generate the pressure baseline, such as averaging, filtering, a curve-fitting, or other processing to generate a baseline. The example of FIG. 3 illustrates a pressure baseline generated using curve fitting. In other examples, other processing can be performed to generate the pressure baseline. In an example, if, at 510, a pulmonary fluid overload event is detected, then, at 525, a pressure baseline can be generated using information sensed or received leading up to or during the detected event.

At 530, a critical time ($T_c$) is computed using the pressure information and the pulmonary fluid information. The critical time ($T_c$) can be computed using the pressure information and the pulmonary fluid information. In an example, the critical time ($T_c$) can be computed as a duration beginning when the pressure information deviates from the pressure baseline and ending when the pressure reaches the critical pressure ($P_c$).

At 535, a filtration index ($K_{fi}$) is computed using the pressure information and the pulmonary fluid information. In an example, the filtration index ($K_{fi}$) can be computed as a function of a slope of the pressure information and a slope of the pulmonary fluid information. In an example, the filtration index can be computed using the slope of the pressure information and the slope of the pulmonary fluid information sensed or received leading up to or during the detected pulmonary fluid overload event.

In other examples, the pulmonary fluid baseline or the pressure baseline can be generated independent of the detection of a pulmonary fluid overload event, and can be used to detect a pulmonary fluid overload event, or can be used to monitor the progress or status of the subject.

Figure 6:
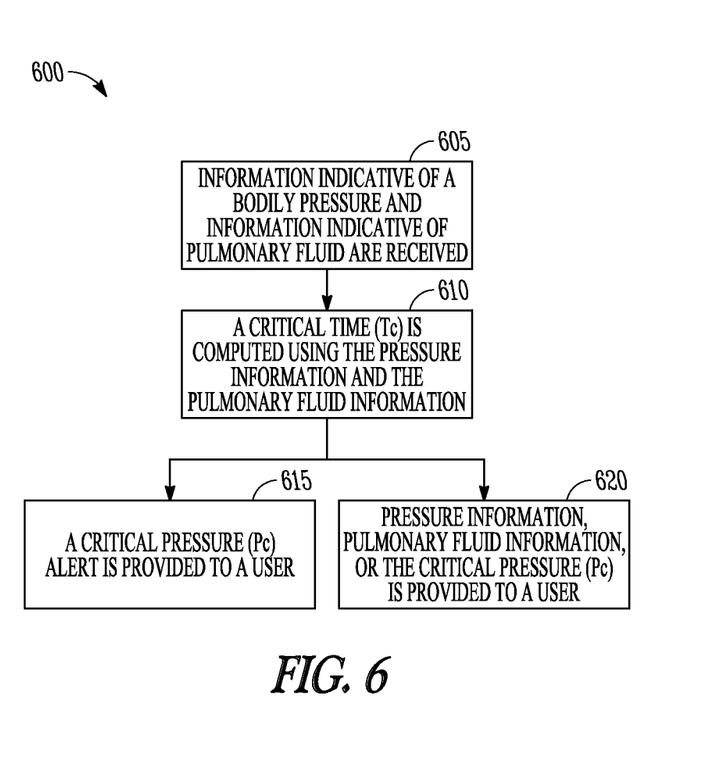
FIG. 6 illustrates generally an example of a method including providing a critical pressure ($P_c$) alert to a user, or providing pressure information, pulmonary fluid information, or the critical pressure ($P_c$) to the user.

FIG. 6 illustrates generally an example of a method 600 including providing a critical pressure ($P_c$) alert to a user, or providing pressure information, pulmonary fluid information, or the critical pressure ($P_c$) to the user.

At 605, information indicative of a bodily pressure and information indicative of pulmonary fluid are received. At 610, a critical pressure ($P_c$) is computed using the pressure information and the pulmonary fluid information.

At 615, a critical pressure ($P_c$) alert is provided to a user. In certain examples, the critical pressure ($P_c$) alert can be provided to the user (e.g., the subject, a clinician, or other user) when the pressure information is indicative that the pressure is approaching the critical pressure ($P_c$) or that the critical pressure ($P_c$) has been reached. In other examples, the other alerts can be provided, such as a pulmonary fluid overload event alert, a pulmonary fluid alert, etc.

In certain examples, an alert can be provided to the user once the pressure information deviates from a pressure baseline, or an alert can be provided to the user if the slope of the pressure information meets or exceeds a threshold (e.g., a slope greater than 0, 0.5, 1, etc.). In other examples, an alert can be provided using the difference between the pressure information and a critical pressure, or using the difference between the pressure information and a critical pressure coupled with the slope of the pressure information.

In other examples, instead of providing an alert to the user, or in addition to providing the alert, a therapy for heart failure or other therapy can be initiated or provided to the subject, or an ongoing therapy can be adjusted.

At 620, pressure information, pulmonary fluid information, or the critical pressure ($P_c$) is provided to the user. In other examples, other information, such as a critical time ($T_c$), can be provided to the user.

Other Examples

In an example, the system 100 can include a display communicatively coupled to the processor 115. The display can be configured to receive information from the processor 115 and provide information to the subject, a clinician, or another user. In an example, the display can be configured to receive physiological information from the processor 115, such as the pressure information, the pulmonary fluid information, the critical pressure, the critical time, the filtration index, or other pressure or fluid points, and provide information to the subject.

In an example, the processor 115 can be configured to compute an estimated critical time ($T_{ec}$). The estimated critical time ($T_{ec}$) can include an estimated time until the pressure reaches the critical pressure ($P_c$). In an example, the processor 115 can be configured to compute the estimated critical time ($T_{ec}$) using the pressure information (e.g., the slope of the pressure information, the current value of the pressure information, or and the difference between the pressure information and the critical pressure ($P_c$). In an example, the critical time ($T_{ec}$) or a critical time ($T_{ec}$) alert can be provided to the user.

In an example, the processor 115 can be configured to compute an estimated decompensation time ($T_{ed}$). The estimated decompensation time ($T_{ed}$) can include an estimated time until the pulmonary fluid information is indicative of the pulmonary fluid associated with a previous pulmonary fluid overload event. In an example, the processor 115 can be configured to compute the estimated decompensation time ($T_{ed}$) using the pulmonary fluid information and the difference between the pulmonary fluid information and the pulmonary fluid associated with the previous pulmonary fluid overload event. In an example, the estimated decompensation time ($T_{ed}$) or an estimated decompensation time ($T_{ed}$) alert can be provided to the user.

In other examples, other information, such as a predicted edema onset time, a predicted time until hospitalization, or other information can be extrapolated using the pressure information, the pulmonary fluid information, or one or more trends of pressure or pulmonary fluid information. In an example, the predicted onset time or can be predicted using one or more trends of pressure or pulmonary fluid information and using information gathered from prior edema or other events, such as prior hospitalization.

In an example, the predicted information can be used to alert or otherwise inform a subject or other user that if the current trend continues, and something is not done to avert it, then edema may begin to develop in an estimated time period (e.g., a certain number of hours, days, etc.), or that hospitalization may be needed or may be expected to occur in another estimated time period (e.g., a certain number of hours, days, etc.).

In an example, the predicting can occur in one or more steps. For example, in a first step, one or more events (e.g., prior events) can be characterized, such as shown in FIG. 2. In certain examples, the one or more prior events can be utilized by quantifying dynamics or metrics leading up to or during a prior pulmonary fluid overload event or eventual hospitalization or other form of treatment. In an example, model parameters can be fit (e.g., using one or more curve fitting or other techniques) to one or more present or past pressure or pulmonary fluid curves.

In the example of FIG. 2, dynamics are quantified leading up to a pulmonary fluid overload event. FIG. 2 illustrates a set of computed metrics, including a critical pressure ($P_c$), a critical time ($T_c$), a slope of the pressure signal, a slope of the pulmonary fluid signal. In other examples, such as that shown in FIG. 7, the time of hospitalization can be detected and stored as well, including a time of hospitalization, a pressure at hospitalization, or a pulmonary fluid (e.g., or an impedance) at hospitalization. In a second step, one or more impending events can be predicted, such as shown in FIG. 7.

Figure 7:
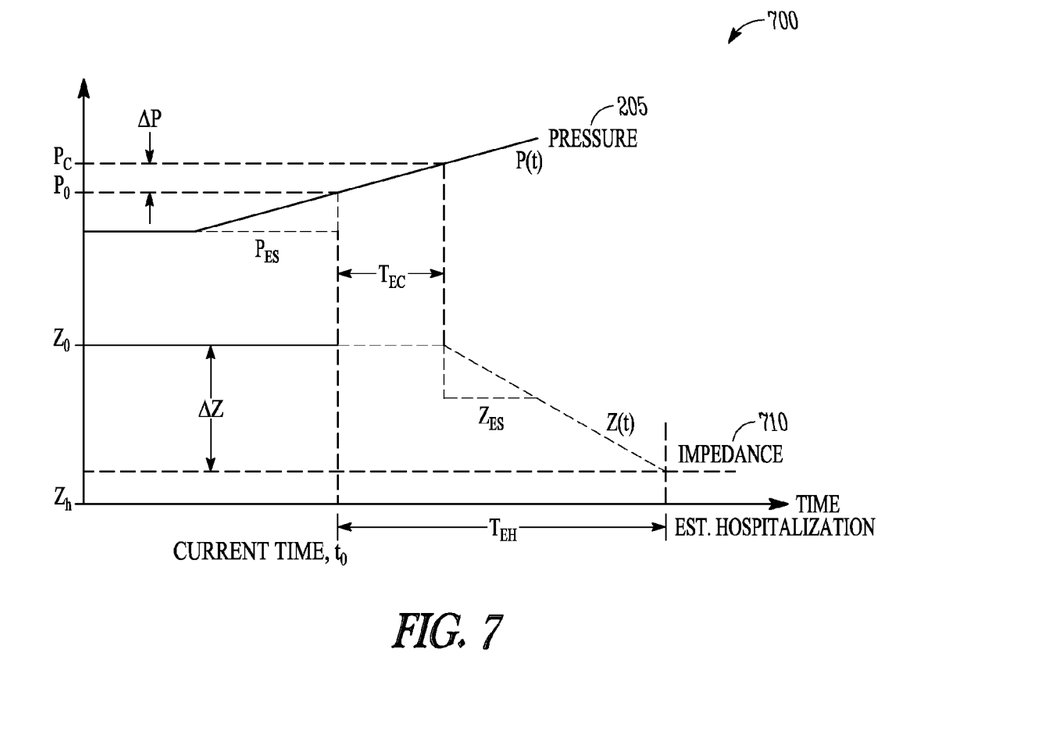
FIG. 7 illustrates generally an example of a relationship between a pressure signal and an impedance signal.

FIG. 7 illustrates generally an example of a relationship 700 between a pressure signal 705 and an impedance signal 710. In an example, to predict an impending event, an increasing pressure trend or other change in pressure or pulmonary fluid information can be monitored. At a current time ($t_0$), an estimated pressure slope ($P_{es}$) can be determined using pressure information, e.g., the pressure signal 705. Using the estimated pressure slope ($P_{es}$) and the difference between the current pressure ($P_0$) and a critical pressure ($P_c$), $\Delta P$, an estimated critical time ($T_{ec}$) can be determined. In an example, the estimated critical time ($T_{ec}$) can include an estimated time before the critical pressure is reached.

In other examples, an estimated pulmonary fluid slope ($Z_{es}$) can be determined using the estimated pressure slope ($P_{es}$), the difference between the current pressure ($P_0$) and a critical pressure ($P_c$), $\Delta P$, or the estimated critical time ($T_{ec}$). In an example, the estimated pulmonary fluid slope ($Z_{es}$) can be computed as a function of the estimated pressure slope ($P_{es}$) (e.g., $Z_{es}=k_{fi}*P_{es}$). In other examples, the shape of the estimated pulmonary fluid slope ($Z_{es}$) can be estimated from the shape of the estimated pressure slope ($P_{es}$), e.g., by integrating area under the curve of a positive estimated pressure.

In an example, an estimated time-to-hospitalization ($T_{eh}$) can be determined using the estimated critical time ($T_{ec}$), the estimated pulmonary fluid slope ($Z_{es}$), or the difference between a current pulmonary fluid ($Z_0$) and a pulmonary fluid at hospitalization ($Z_h$).

Some Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products.

Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system for use with a physiologic pressure sensor, the system comprising:
    a processor comprising:
        a pressure sensor input configured to receive information indicative of a bodily pressure from the physiologic pressure sensor; and
        an impedance sensor input configured to receive impedance information indicative of a pulmonary fluid level;
    wherein the processor is configured to generate a pressure baseline using the information indicative of the bodily pressure received from the physiologic pressure sensor;
    wherein the processor is configured to generate a pulmonary fluid level baseline using the impedance information indicative of the pulmonary fluid level;
    wherein the processor is configured to identify a critical pressure ($P_c$) using the information indicative of the bodily pressure received from the physiologic pressure sensor and the received impedance information indicative of the pulmonary fluid level information, wherein the critical pressure ($P_c$) is the pressure at which the received impendence falls below the pulmonary fluid level baseline; and
    wherein the processor is configured to compute a critical time (Tc) using the information indicative of the bodily pressure received from the physiologic pressure sensor and the received impedance information indicative of the pulmonary fluid level, wherein the critical time (Tc) defines a duration beginning when the information indicative of the bodily pressure deviates from the pressure baseline and ending when the pressure reaches the critical pressure (Pc).

2. The system of claim 1, wherein the processor comprises an event detector input configured to receive information about a detected pulmonary fluid overload event, and wherein the processor is configured to identify the critical pressure ($P_c$) using the information indicative of the bodily pressure received from the physiologic pressure sensor leading up to or during the detected event and the received impedance information indicative of the pulmonary fluid level leading up to or during the detected event.

3. The system of claim 1, wherein the processor comprises an event detector input configured to receive information about a detected pulmonary fluid overload event, and wherein the processor is configured to compute the critical time ($T_c$) using the information indicative of a bodily pressure received from the physiologic pressure sensor leading up to or during the detected event and the received impedance information indicative of the pulmonary fluid level leading up to or during the detected event.

4. The system of claim 1, wherein the processor is configured to compute an estimated pressure slop (Pes) using the information indicative of the bodily pressure received from the physiologic pressure sensor, and wherein the processor is configured to compute an estimated critical time (Tec) using a current pressure determined using the information indicative of the bodily pressure received from the physiologic pressure sensor, the critical pressure (Pc), and the computed estimated pressure slope (Pes).

5. The system of claim 4, wherein the processor is configured to use the estimated critical time (Tec) to predict an impending patient event.

6. The system of claim 1, wherein the processor is configured to compute a filtration index ($K_{fi}$) as a function of a slope of the information indicative of the bodily pressure received from the physiologic pressure sensor and a slope of the impendence information indicative of the pulmonary fluid level.

7. The system of claim 6, including an event detector input configured to detect a pulmonary fluid overload event, wherein the processor is configured to compute the filtration index ($K_{fi}$) using the information indicative of the bodily pressure received from the physiologic pressure sensor leading up to or during the detected event and the received impedance information indicative of the pulmonary fluid level leading up to or during the detected event.

8. The system of claim 7, wherein the detected pulmonary fluid overload event includes at least one of a user-confirmed pulmonary fluid overload event or an automatically detected pulmonary fluid overload event, wherein the user-confirmed event includes at least one of a hospitalization or a change in medication, and wherein the automatically detected event includes at least one of information exceeding a threshold or a baseline, the information including at least one of a value or a slope.

9. The system of claim 1, comprising the physiologic pressure sensor, wherein the physiologic pressure sensor is an implantable chronic pulmonary artery pressure sensor configured to be fixed to a location within the pulmonary artery;
    wherein the pressure sensor input is configured to chronically receive information indicative of a pulmonary artery pressure of a pulmonary artery using the implantable chronic pulmonary artery pressure sensor.

10. The system of claim 1, wherein the processor is configured to provide a critical pressure (Pc) alert to a user when the information indicative of the bodily pressure received from the physiologic pressure sensor indicates that the pressure is approaching the critical pressure ($P_c$) or that the critical pressure (Pc) has been reached.

11. The system of claim 1, including:
    a display, communicatively coupled to the processor, the display configured to receive information about at least one of the information indicative of the bodily pressure received from the physiologic pressure sensor, the received information indicative of the pulmonary fluid level, or the critical pressure (P$_c$), and wherein the display is configured to provide the received information to a user.

12. The system of claim 1, wherein the processor is configured to use the critical time (Tc) to generate a therapy requirement alert.

13. The system of claim 1, wherein the processor is configured to trend the critical time (Tc) over time, wherein the trend of the critical time (Tc) over time is indicative of a patient disease status progression.

14. The system of claim 1, wherein the critical time (Tc) indicates a time-to-failure of a patient pulmonary compensatory mechanism.

15. The system of claim 1, wherein the critical time (Tc) defines a duration beginning when the information indicative of the bodily pressure exceeds the pressure baseline by a threshold amount and ending when the pressure reaches the critical pressure (Pc).

16. A system for use with a physiologic pressure sensor, the system comprising:
 a processor comprising:
  a pressure sensor input configured to receive information indicative of a bodily pressure from the physiologic pressure sensor; and
  an impedance sensor input configured to receive impedance information indicative of a pulmonary fluid level;
 wherein the processor is configured to generate a pressure baseline using the information indicative of the bodily pressure received from the physiologic pressure sensor;
 wherein the processor is configured to generate a pulmonary fluid level baseline using the impedance information indicative of the pulmonary fluid level;
 wherein the processor is configured to identify a critical pressure (P$_c$) using the information indicative of the bodily pressure received from the physiologic pressure sensor and the received impedance information indicative of the pulmonary fluid level information, wherein the critical pressure (P$_c$) is a pressure at which the received impedance information indicative of the pulmonary fluid level falls below the pulmonary fluid level baseline; and
 wherein the processor is configured to compute an estimated pressure slope (Pes) using the information indicative of the bodily pressure received from the physiologic pressure sensor, and wherein the processor is configured to compute an estimated critical time (Tec) using a current pressure determined using the information indicative of the bodily pressure received from the physiologic pressure sensor, the critical pressure (Pc), and the computed estimated pressure slope (Pes), and wherein the processor is configured to use the estimated critical time (Tec) to predict an impending patient event.

17. The system of claim 16, wherein the processor is further configured to output a signal representing the computed estimated critical time (Tec) to a display.

18. The system of claim 16, wherein the processor is configured to compute an estimated pulmonary fluid slope (Zes), wherein the processor is configured to compute an estimated time-to-hospitalization (Teh) using the estimated pulmonary fluid slope (Zes), and wherein the processor is further configured to output a signal representing the computed estimated time-to-hospitalization (Teh) to a display.

19. The system of claim 18, wherein the processor is configured to compute a filtration index (K$_{fi}$) as a function of a slope of the information indicative of the bodily pressure received from the physiologic pressure sensor and a slope of the received impedance information indicative of the pulmonary fluid level, and wherein the estimated pulmonary fluid slope (Zes) equals the filtration index (K$_{fi}$) multiplied by the estimated pressure slope (Pes).

20. A system for use with a physiologic pressure sensor, the system comprising:
 a processor comprising:
  a pressure sensor input configured to receive information indicative of a bodily pressure from the physiologic pressure sensor; and
  an impedance sensor input configured to receive impedance information indicative of a pulmonary fluid level;
 wherein the processor is configured to generate a pressure baseline using the information indicative of the bodily pressure received from the physiologic pressure sensor;
 wherein the processor is configured to generate a pulmonary fluid level baseline using the impedance information indicative of the pulmonary fluid level;
 wherein the processor is configured to identify a critical pressure (P$_c$) using the information indicative of the bodily pressure received from the physiologic pressure sensor and the received impedance information indicative of the pulmonary fluid level information, wherein the critical pressure (P$_c$) is a pressure at which the received impedance information indicative of the pulmonary fluid level falls below the pulmonary fluid level baseline; and
 wherein the processor is configured to compute a critical time (Tc) using the information indicative of the bodily pressure received from the physiologic pressure sensor and the received impedance information indicative of the pulmonary fluid level, wherein the critical time (Tc) defines a duration beginning when the information indicative of the bodily pressure deviates from the pressure baseline and ending when the pressure reaches the critical pressure (Pc);
 wherein the processor is configured to compute a filtration index (K$_{fi}$) as a function of a slope of the information indicative of the bodily pressure received from the physiologic pressure sensor leading up to or during a pulmonary fluid overload event and a slope of the impedance information indicative of the pulmonary fluid level leading up to or during the pulmonary fluid overload event, wherein the pulmonary fluid overload event includes at least one of a user-confirmed pulmonary fluid overload event or an automatically detected pulmonary fluid overload event, wherein the user-confirmed event includes at least one of a hospitalization or a change in medication, and wherein the automatically detected event includes at least one of information exceeding a threshold or a baseline, the information including at least one of a value or a slope.

* * * * *